United States Patent [19]

Sjöovist

[11] Patent Number: 4,656,027

[45] Date of Patent: Apr. 7, 1987

[54] PHARMACEUTICAL MIXTURE

[75] Inventor: Rolf I. Sjöovist, Gnesta, Sweden

[73] Assignee: Astra Lakemedel Aktiebolag, Sodertalje, Sweden

[21] Appl. No.: 668,168

[22] Filed: Nov. 2, 1984

Related U.S. Application Data

[63] Continuation-in-part of Ser. No. 383,148, May 28, 1982, abandoned.

[30] Foreign Application Priority Data

Jun. 18, 1981 [SE] Sweden ................................. 8103843

[51] Int. Cl.$^4$ .......................... A61K 9/22; A61K 9/36; A61K 9/52; A61K 9/62
[52] U.S. Cl. ..................................... 424/495; 424/497
[58] Field of Search ..................................... 424/35, 19

[56] References Cited

U.S. PATENT DOCUMENTS

| | | | |
|---|---|---|---|
| 4,101,651 | 7/1978 | Kobayashi et al. | 424/35 |
| 4,177,254 | 12/1979 | Khan et al. | 424/35 |
| 4,205,060 | 5/1980 | Monsimer et al. | 424/35 |
| 4,261,970 | 4/1981 | Ogawa et al. | 424/35 |
| 4,321,253 | 3/1982 | Beatty | 424/35 |

FOREIGN PATENT DOCUMENTS 80129224 3/1979 Japan .

OTHER PUBLICATIONS

Lachman et al., "The Theory and Practice of Industrial Pharmacy".

Primary Examiner—Stanley J. Friedman
Attorney, Agent, or Firm—Brumbaugh, Graves, Donohue & Raymond

[57] ABSTRACT

The present invention is concerned with masking bad taste in pharmaceutical preparations containing encapsulated drugs with bad taste. The object of the invention is achieved by including a basic substance in the preparation.

11 Claims, No Drawings

PHARMACEUTICAL MIXTURE

This application is a continuation-in-part of application Ser. No. 383,148, filed on May 28, 1982, now abandoned.

TECHNICAL FIELD

The present invention is concerned with an oral pharmaceutical preparation primarily but not solely for pediatric use, containing an active substance with bad taste, in which preparation the bad taste has been masked.

The object of the present invention is to provide a powder for mixture, wherein the bad taste of the active ingredient has been masked without loosing any pharmacodynamic properties of the mixture.

BACKGROUND ART

As tablets are inconvenient for pediatric use other types of formulation have to be chosen. An alternative form of administration for pediatric use is a solution or a suspension of the active principle in water—a mixture. The dry powder including the active principle and adjuvants which is to be dissolved or suspended is henceforward called dry powder for mixture.

The preparation is stored as a dry powder. Before administration the dry powder is dissolved or suspended in water giving rise to a liquid formulation for oral administration—a mixture.

Hitherto bitter medicines have been coated with ethyl cellulose alone or together with wax to mask their bad taste (microencapsulation). The polymer ethyl cellulose is not pH sensitive and is not soluble in water. Applied on granulates of a drug it retards the rate of dissolution.

The main way to control drug dissolution from this type of microcapsule is the amount of polymer applied. In order to mask taste, the rate of dissolution should be very slow, but from a bioavailability point of view it should be as fast as possible. However, when applying a coating thin enough to be acceptable from the bioavailability point of view it is unacceptable in view of its insufficiency to mask the bad taste.

It has also been suggested (Japanese Kokai No. 80 129,224) to mask bitter taste by coating the granules with a coating agent containing ethyl cellulose and an antacid. This method has the drawback of causing difficulties when producing the preparation, particularly when producing larger quantities.

DISCLOSURE OF THE INVENTION

The present invention makes it possible to overcome the difficulties attached to the methods of preparing formulations on microencapsulated bitter drugs previously used by adding a basic substance to the encapsulated drug powder or adding it within the capsules.

The invention provides suspensions of the dry powder with improved stability properties.

The drug shall be in a form which is soluble or easily soluble at a low pH and unsoluble or difficult to dissolve at a high pH. For drugs which can be used in accordance with this invention it means that they are soluble or easily soluble in salt form and unsoluble or difficult to dissolve in base form.

Drugs that can be used in the formulation according to this invention are for instance Clobutinolum, Noscapinum, Bromhexidinum, Terbutalinum, Chinidinum, Prometazinum, Diphenhydraminum, Brompheniraminum, Sulfadiazinum, Bacampicillinum, Pivampicillinum, Tetracyclinum, Erythromycinum, Trimethoprimum, Dextropropoxyphenum and Chloroquinum.

The preferred drug is becampicillin hydrochloride (1'-ethoxycarbonyloxyethyl 6-[D(−)-2-amino-2-phenylacetamido]-penicillanate hydrochloride), other epimeric forms and the racemic form of bacampicillin hydrochloride.

The drugs mentioned above are used in base or salt form.

The following salts of the drugs mentioned above can be used:

Acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, clycollylarsanilate, hexylresorcinate, hydrabamine, hydrobromide, hydrochloride, hydroxynaphthoate, iodide, isethionate, lactate, lactobionate, malate, maleate, mandelate, mysylate, methylbromide, methylnitrate, methylsulfate, mucate, napsylate, nitrate, pamoate (embonate), pantothenate, phosphate/diphosphate, polygalacturonate, salicylate, stearate, subacetate, succinate, sulfate, tannate, tartrate, teoclate, triethiodide.

The encapsulation of the drug can be achieved in the form of microcapsules, but the encapsulation is not restricted to the micro size. Microencapsulation of the drug can be achieved e.g. by coacervation or by fluidized bed coating.

By coacervation coating, drug particles are added to a solution of a polymer in a solvent. The polymer is forced to precipitate on the drug particles either by adding salts or by cooling a preheated solution. The coated particles are then washed and dried.

By fluidized bed coating drug particles are added to a fluidized bed apparatus and the polymer is applied on the drug particles by spraying a polymer solution which deposits the polymer on the surface of the drug particles.

The encapsulation of the drug can be achieved with a microporous unsoluble cover, such as cellulosic polymers (e.g. ethylcellulose) and polyvinyl polymers (e.g. polyvinylacetate, polyvinylchloride).

Also an acid soluble polymer containing an amine function, e.g. a copolymer of dimethylaminoethyl methacrylate and methylmethacrylate, such as Eudragit ® E 100, can be used according to the formulation of the invention to encapsulate the drug.

Basic substances according to the invention are carbonates, e.g. sodium bicarbonate; phosphates, e.g. disodium mono hydrogenphosphate, and dipotassium hydrogenphosphate; citrates, e.g. trisodium citrate; hydroxides e.g. magnesium dihydroxide trizma which has the formula:

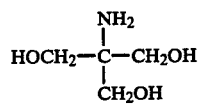

The preferred basic substance is sodium bicarbonate.

The amount of basic substance in the dry powder preparation is best represented as a molar ratio between basic substance and drug. This ratio is 0.2–10, preferably 0.5–2.

In one embodiment of the invention bacampicillin hydrochloride (BAPC) is encapsulated in an unsoluble, microporous polymer, such as ethyl cellulose and sodium bicarbonate and customary adjuvants are added to make a dry powder for mixture.

In another embodiment of the invention BAPC is encapsulated in a polymer soluble in acid, such as Eudragit ® E 100 and sodium bicarbonate and customary adjuvants are added to make a dry powder for mixture.

In a further embodiment of the invention sodium bicarbonate is encapsulated together with the active substance within the polymeric shell.

BEST MODE OF CARRYING OUT THE INVENTION

The preferred formulation is bacampicillin hydrochloride encapsulated in ethyl cellulose and with addition of sodium bicarbonate.

The following examples used ethyl cellulose having one of the following specifications:

| (a) | Description | A free-flowing, white to light tan powder Solubility (20° C.) In water - insoluble In alcohol - freely soluble In toluene - freely soluble |
|---|---|---|
| | Requirements | |
| 1 | Appearance | A free-flowing, white to light tan powder |
| 2 | IR-spectrum | Conforms with a reference spectrum |
| 3 | Viscosity | 80 to 110 cps (5% solution in 80 parts toluene and 20 parts of ethanol (w/w) at 25° C.) |
| 4 | Heavy metals | Corresponding to not more than 40 µg Pb/g |
| 5 | Lead | Not more than 10 µg/g |
| 6 | Arsenic | Not more than 3 µg/g |
| 7 | Loss on drying | Not more than 3.0% (105° C., 2 h) |
| 8 | Residue on ignition | Not more than 0.4% |
| 9 | Ethoxy groups | 44.0 to 51.0% calculated on the dried basis |
| (b) | Description | A free-flowing, white to light tan powder Solubility (20° C.) In water - insoluble In alcohol - freely soluble In toluene - freely soluble |
| | Requirements | |
| 1 | Appearance | A free-flowing, white to light tan powder |
| 2 | IR-spectrum | Conforms with a reference spectrum |
| 3 | Viscosity | 9–11 cps (5% solution in 80 parts toluene and 20 parts of ethanol (w/w) at 25° C.) |
| 4 | Heavy metals | Corresponding to not more than 40 µg Pb/g |
| 5 | Lead | Not more than 10 µg/g |
| 6 | Arsenic | Not more than 3 µg/g |
| 7 | Loss on drying | Not more than 3.0% (105° C., 2 h) |
| 8 | Residue on ignition | Not more than 0.4% |
| 9 | Ethoxy groups | 44.0 to 51.0% calculated on the dried basis |

These specifications are meant only by way of example and any conventional microporous unsoluble coatings having a viscosity of 9 to 110 cps such as ethyl cellulose, polyvinylacetate, polyvinylchloride or a copolymer of dimethylaminoethyl methacrylate and methylmethacrylate are suitable for use in this invention.

WORKING EXAMPLES

Example 1

Dry powder for mixture 100 g of the dry powder contains

| | |
|---|---|
| Bacampicillin hydrochloride microcapsules corresponding to bacampicillin hydrochloride 100% | 5.00 g |
| Sodiumbicarbonate | 1.00 g |
| Sodiumcarboxymethyl cellulose | 0.69 g |
| Flavouring agents | 2.92 g |
| Sugars | to 100.00 g |

The powders are mixed together giving a dry powder for mixture.

Example 2

Influence of microencapsulation and the addition of sodium bicarbonate upon taste of bacampicillin hydrochloride The taste of different products has been evaluated by a taste panel consisting of 24 people. The tests have been carried out in a randomized double-blind crossover fashion. The tests have been of triangle and preference types. In the preference test the different products have been compaired to a standard product of a penicillin with acceptable taste.

The results from those tests can be summed up in the following way

| Type of dry formulation | Taste |
|---|---|
| Plain bacampicillin HCl | Extremely bad |
| Bacampicillin HCl microcapsules | Not acceptable |
| Bacampicillin HCl microcapsules + sodium bicarbonate as buffer according to the invention | Acceptable |

It is obvious that the taste is improved by using microcapsules of the bad tasting drug which are suspended in media which contain a buffering substance.

Leakage of bacampicillin hydrochloride from microcapsules in reconstituted suspension In this study a composition according to Example 1 except flavouring agents was used. At low pH sodium bicarbonate was replaced by citrate buffer. 5 grams of the dry powder was suspended with 5 ml of water. After ten minutes the microcapsules were filtered off and the filtrate was analysed for drug content.

| Results | % Leakage |
|---|---|
| Composition with sodium bicarbonate (pH = 7.5) according to the invention | 0.6 |
| Composition with citrate buffer (pH = 4.0) | 1.8 |

This finding verifies that a low leakage results in a better taste than a product with more leakage according to the taste tests which have been performed.

Dissolution of bacampicillin hydrochloride from microcapsules filtered off from a reconstituted suspension An experiment was performed in order to simulate the behaviour of the composition according to the invention in gastric environment. Microcapsules containing bacampicillin hydrochloride in the composition in Example 1 were filtered off and washed with 0.1M sodiumbicarbonate solution. Dissolution of the microcapsules was performed in a flow-through apparatus. The dissolution medium was simulated gastric fluid without enzymes (pH 1.2).

Result: There was no difference in dissolution rate between microcapsules which had been in contact with the suspension and with nontreated microcapsules.

This finding indicates that the constituents of the suspension will not affect the dissolution characteristics of the microcapsules.

Bioavailability of bacampicillin hydrochloride microcapsule suspension, according to the invention Bioavailability of this suspension has been studied on 12 adult volunteers. The dose of the suspension was 400 mg of the drug. Blood samples were collected from each volunteer and analysed for ampicillin contents (Bacampicillin is a prodrug of ampicillin and is readily converted to ampicillin during the process of absorption). Bioavailability studies of bacampicillin hydrochloride 400 mg tablets have been performed at several different occasions. A typical result is shown.

| Results | AUC (ml/l · h) | T max (hrs) | Ind. C max (mg/l) |
|---|---|---|---|
| Tablets | 12.2 | 0.88 | 8.0 |
| Suspension | 13.8 | 0.75 | 8.2 |

AUC = mean of area under the plasma concentration versus time curve
T max = median of the time required to reach plasma concentration maximum
Ind C max = the mean of individual plasma concentration maximum According to the parameters given there is no great difference between the two different formulations of bacampicillin hydrochloride. This means that the suspension has the same magnitude of bioavailability as the conventional dosage form, the tablet.

Conclusion

The experiments described in this example have shown that a mixture of bacampicillin hydrochloride based on ethyl cellulose microcapsules can be obtained. The suspension has a very low leakage of the penicillin in the formulation but upon dissolution of the microcapsules in vitro in an acidic environment the drug will dissolve rapidly.

It has been possible to obtain a formulation with above mentioned properties due to addition of a small amount of sodium bicarbonate which dramatically decreased the leakage ot the penicillin in the formulation. The decreased leakage of the bitter substance means that the formulation will have no or a negligible bitter taste.

Example 3

Stability of bacampicillin hydrochloride microcapsule supsension 64 g of dry powder from Example 1 for mixture was reconstituted with 39 ml of water. The obtained suspensions were stored in a refrigerator (5° C.) for 14 days and in room temperature (25° C.) for 8 days. The content was analyzed and calculated in percent of the initial content. Five batches of dry mixture was tested.

| Temperature °C. | Time days | Content % |
|---|---|---|
| 5 | 14 | 97.6 |
| 25 | 4 | 95.2 |
| 25 | 8 | 91.8 |

I claim:

1. A method for preparing a dry powder for use as a pharmaceutical preparation which comprises mixing a pharmaceutically acceptable basic substance selected from the group consisting of sodium bicarbonate, disodium mono hydrogenphosphate, dipotassium hydrogenphosphate, trisodium citrate, magnesium dihydroxide and trizma with a bad tasting drug, said drug being in a form insoluble at high pH, and said basic substance being present in a mole ratio of basic substance to drug of 0.2–10, and encapsulating the mixture in a material consisting essentially of a water insoluble polymer selected from the group consisting of ethylcellulose, polyvinyl acetate, polyvinyl chloride and a copolymer of dimethylaminoethyl methacrylate and methyl methacrylate, wherein the encapsulated material is present in an amount that allows bioavailability and which in combination with the basic substance is sufficient to mask the taste of the drug.

2. A method of preparing a pharmaceutical mixture according to claim 1 wherein the water insoluble polymer is ethylcellulose.

3. A method according to claim 1, wherein the drug is selected from the group consisting of Bacampicillin, Clobutinolum, Noscapinum, Bromhexidinum, Terbutalinum, Chinidinum, Prometazinum, Diphenhydraminum, Brompheniraminum, Sulfadiazinum, Pivampicillinum, Tetracyclinum, Erythromycinum, Trimethroprim, Dextropropoxyphenum and Chloroquinum or pharmaceutically acceptable salts thereof.

4. A dry powder produced by the process of claim 1 for use as a pharmaceutical preparation comprising a pharmaceutically acceptable basic substance and a bad tasting drug in a form insoluble at a high pH, both encapsulated in a material consisting essentially of a water insoluble polymer selected from the group consisting of ethyl cellulose, polyvinyl acetate, polyvinyl chloride and a copolymer of dimethylaminoethyl methacrylate and methyl methacrylate, wherein the basic substance is present in a mole ratio of basic substance to drug of 0.2–10.

5. A dry powder according to claim 4, wherein the drug is selected from the group consisting of bacampicillin, Clobutinolum, Noscapinum, Bromhexidinum, Terbutalinum, Chinidinum, Prometazinum, Diphenhydraminum, Brompheniraminum, Sulfadiazinum, Pivampicillinum, Tetracylinum, Erythromycinum, Trimethoprim, Dextropropoxyphenum, and Chloroquinum, or pharmaceutically acceptable salts thereof.

6. A dry powder according to claim 4, wherein the basic substance is sodium bicarbonate.

7. A method of preparing a dry powder for use as a pharmaceutical preparation which comprises mixing a pharmaceutically acceptable basic substance selected from the group consisting of sodium bicarbonate, disodium mono hydrogenphosphate, dipotassium hydrogenphosphate, trisodium citrate, magnesium dihydroxide and trizma with a bad tasting drug encapsulated in a material consisting essentially of a water-insoluble polymer selected from the group consisting of ethylcellulose, polyvinyl acetate, polyvinyl chloride and a copolymer of dimethylaminoethyl methacrylate and methylmethacrylate, said drug being present in a form insoluble at high pH, said basic substance being present in a mole ratio of basic substance to drug of 0.2–10, wherein the encapsulated material is present in an amount that allows bioavailability and which in combination with the basic substance is sufficient to mask the taste of the drug.

8. A method according to claim 7, wherein the drug is selected from the group consisting of Bacampicillin, Clobutinolum, Noscapinum, Bromhexidinum, Terbutalinum, Chinidinum, Prometazinum, Diphenhydraminum, Brompheniraminum, Sulfadiazinum, Pivampicillinum, Tetracyclinum, Erythromycinum, Trimethroprim, Dextropropoxyphenum and Chloroquinum or pharmaceutically acceptable salts thereof.

9. A dry powder produced by a process according to claim 7 for use as a pharmaceutical preparation comprising
   a pharmaceutically acceptable basic substance, and a bad-tasting drug encapsulated in a material consisting essentially of a water-insoluble polymer selected from the group consisting of ethyl cellulose, polyvinyl acetate, polyvinyl chloride, and a copolymer of dimethylaminoethyl methacrylate and methylmethacrylate,
   wherein the drug is in a form insoluble at high pH, and the basic substance is present in a mole ratio of basic substance to drug of 0.2–10.

10. A dry powder according to claim 9 wherein the drug is selected from the group consisting of bacampicillin, Clobutinolum, Noscapinum, Bromhexidinum, Terbutalinum, Chinidinum, Prometazinum, Diphenhydraminum, Brompheniraminum, Sulfadiazinum, Pivampicillinum, Tetracyclinum, Erythromycinum, Trimethoprim, Dextropropoxyphenum, and Chloroquinum, or pharmaceutically acceptable salts thereof.

11. A dry powder according to claim 9 wherein the basic substance is sodium bicarbonate.

* * * * *

UNITED STATES PATENT AND TRADEMARK OFFICE
CERTIFICATE OF CORRECTION

PATENT NO. : 4,656,027

DATED : April 7, 1987

INVENTOR(S) : Sjoqvist

It is certified that error appears in the above-identified patent and that said Letters Patent is hereby corrected as shown below:

First page, Item 75, "Sjöovist" should read --Sjöqvist--;

Col. 1, line 16, "loosing" should read --losing--;

Col. 2, line 6, "becampicillin" should read --bacampicillin--;

Col. 2, line 58, after "dihydroxide" insert --and--;

Col. 5, line 58, "ot" should read --of--; and

Col. 5, line 65, "supsension" should read --suspension--.

Signed and Sealed this

Fifteenth Day of September, 1987

Attest:

DONALD J. QUIGG

*Attesting Officer*    *Commissioner of Patents and Trademarks*